United States Patent
Matsunaga et al.

(10) Patent No.: US 10,729,409 B2
(45) Date of Patent: Aug. 4, 2020

(54) MEDICAL IMAGE PROCESSING APPARATUS AND MEDICAL IMAGE PROCESSING METHOD

(71) Applicant: TOSHIBA MEDICAL SYSTEMS CORPORATION, Otawara-Shi (JP)

(72) Inventors: Satoshi Matsunaga, Nasushiobara (JP); Yoshitaka Mine, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 390 days.

(21) Appl. No.: 15/657,846

(22) Filed: Jul. 24, 2017

(65) Prior Publication Data
US 2018/0028156 A1    Feb. 1, 2018

(30) Foreign Application Priority Data

Jul. 26, 2016   (JP) ................................ 2016-146715
Jul. 20, 2017   (JP) ................................ 2017-140686

(51) Int. Cl.
*A61B 8/00*    (2006.01)
*A61B 8/08*    (2006.01)
(Continued)

(52) U.S. Cl.
CPC .......... *A61B 8/5207* (2013.01); *A61B 8/4254* (2013.01); *A61B 8/461* (2013.01); *A61B 8/483* (2013.01); *G06T 11/001* (2013.01); *G06T 11/60* (2013.01); *G06T 15/08* (2013.01); *A61B 8/14* (2013.01); *A61B 8/463* (2013.01); *A61B 8/485* (2013.01); *A61B 8/488* (2013.01); *G06T 2210/41* (2013.01)

(58) Field of Classification Search
CPC .................................................... A61B 8/4254
See application file for complete search history.

(56) References Cited

U.S. PATENT DOCUMENTS

2007/0255137 A1*  11/2007  Sui ........................... A61B 8/00
                                                      600/443
2015/0182191 A1    7/2015  Caluser et al.
2016/0296769 A1*  10/2016  Barthe ..................... A61N 7/00

FOREIGN PATENT DOCUMENTS

CN        101002681 A        7/2007
CN        102081697 A        6/2011
JP        2007-319492        12/2007

OTHER PUBLICATIONS

Chinese Office Action dated Nov. 28, 2019, issued in Chinese Patent Application No. 201710605871.X.
(Continued)

*Primary Examiner* — Rochelle D Turchen
(74) *Attorney, Agent, or Firm* — Oblon, McClelland, Maier & Neustadt, L.L.P.

(57) ABSTRACT

According to one embodiment, a medical image processing apparatus includes the processing circuitry. The processing circuitry generates an image from volume data. The volume data is generated based on echo data acquired while the ultrasonic probe is moved and output of a positional sensor provided on the ultrasonic probe. The processing circuitry further generates an indicator indicating speed of the ultrasonic probe and recommended speed range of moving the ultrasonic probe. The speed of the ultrasonic probe is calculated based on the output of the positional sensor. The processing circuitry causes a display to display the image and the indicator.

10 Claims, 11 Drawing Sheets

(51) Int. Cl.
*G06T 15/08* (2011.01)
*G06T 11/00* (2006.01)
*G06T 11/60* (2006.01)
*A61B 8/14* (2006.01)

(56) References Cited

OTHER PUBLICATIONS

Chinese Office Action dated May 25, 2020, issued in Chinese Patent Application No. 201710605871.X.

* cited by examiner

| A-PLANE | x-y PLANE |
|---------|-----------|
| B-PLANE | y-z PLANE |
| C-PLANE | z-x PLANE |

| A-PLANE | SCANNING PLANE |
|---------|----------------|
| B-PLANE | y-z PLANE |
| C-PLANE | z-x PLANE |

MEDICAL IMAGE PROCESSING APPARATUS AND MEDICAL IMAGE PROCESSING METHOD

CROSS-REFERENCE TO RELATED APPLICATIONS

This application claims the benefit of priority of Japanese Patent Application No. 2016-146715, filed Jul. 26, 2016, and Japanese Patent Application No. 2017-140686, filed Jul. 20, 2017, the entire contents of all of which are incorporated herein by reference.

FIELD

Embodiments described herein relate generally to a medical image processing apparatus and a medical image processing method.

BACKGROUND

As a method of generating three-dimensional ultrasonic image data (i.e., ultrasonic volume data, hereinafter, referred to as volume data) by using an ultrasonic diagnostic apparatus, there is a known method of generating volume data by arranging a series of ultrasonic tomographic images which are acquired by imaging an object at a predetermined frame rate while an ultrasonic probe is being moved. In this method, it is important for acquiring volume data having sufficiently uniform data density that an ultrasonic probe is moved at a constant velocity. When an ultrasonic probe is moved at a constant velocity and imaging is performed at a predetermined frame rate, it is possible to acquire isochronal ultrasonic tomographic images and volume data with uniform data density.

For instance, in the case of generating respective images of arbitrary cross-sections from volume data, image quality of these cross-sectional images depends on data density of the corresponding cross-sections in the volume data. Data density of volume data depends on velocity of an ultrasonic probe. Thus, for instance, when a velocity component of an ultrasonic probe in the direction along the target cross-section to be extracted in the form of an image increases, data density within this target cross-section is reduced and image quality of this target cross-section is deteriorated. Hence, in order to acquire a cross-sectional image with satisfactory image quality from volume data, it is desirable to move an ultrasonic probe at a speed within a predetermined speed range.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4A is viewed in the direction of the y-axis;

DETAILED DESCRIPTION

Hereinbelow, a description will be given of a medical image processing apparatus and a medical image processing method according to embodiments of the present invention with reference to the drawings.

In general, according to one embodiment, a medical image processing apparatus includes the processing circuitry. The processing circuitry generates an image from volume data. The volume data is generated based on echo data acquired while the ultrasonic probe is moved and output of a positional sensor provided on the ultrasonic probe. The processing circuitry further generates an indicator indicating speed of the ultrasonic probe and recommended speed range of moving the ultrasonic probe. The speed of the ultrasonic probe is calculated based on the output of the positional sensor. The processing circuitry causes a display to display the image and the indicator.

First Embodiment

Figure 1:
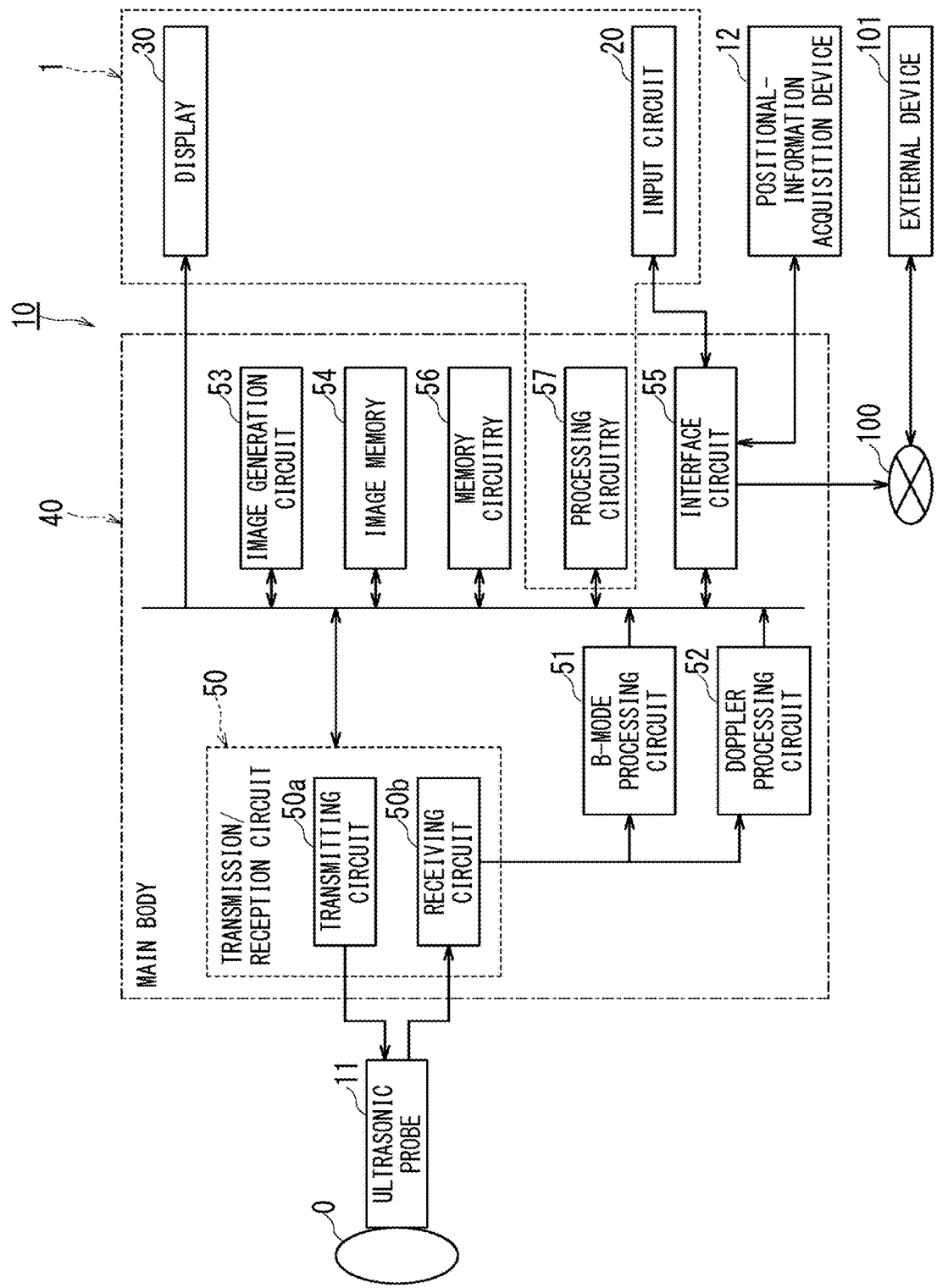
FIG. 1 is a block diagram illustrating a configuration example of an ultrasonic diagnostic apparatus which is equipped with the medical image processing apparatus according to the first embodiment of the present invention.

FIG. 1 is a block diagram illustrating a configuration example of an ultrasonic diagnostic apparatus 10 which is equipped with the medical image processing apparatus 1 according to the first embodiment of the present invention. The ultrasonic diagnostic apparatus 10 includes an ultrasonic probe 11, a positional-information acquisition device 12, an input circuit 20, a display 30, and a main body 40.

In the present embodiment, the medical image processing apparatus 1 is included in the ultrasonic diagnostic apparatus 10 such that the input circuit 20, the display 30, and processing circuitry 57 of the main body 40 constitute the medical image processing apparatus 1.

The ultrasonic probe 11 is equipped with plural ultrasonic transducers (i.e., piezoelectric vibrators). Each of those plural ultrasonic transducers generates an ultrasonic wave on the basis of a drive signal supplied from the main body 40. The ultrasonic probe 11 forms a beam-like ultrasonic wave (i.e., ultrasonic beam) by converging ultrasonic waves outputted from the plural ultrasonic transducers, transmits this ultrasonic beam to inside of a body of an object O, and receives an echo signal (i.e., reflected-wave signal) from the object O so as to convert the echo signal into an electric signal. Moreover, the ultrasonic probe 11 includes components such as a matching layer provided on the ultrasonic transducers and a backing material which prevents ultrasonic waves from propagating toward the back side of the ultrasonic transducers.

When an ultrasonic beam is transmitted from the ultrasonic probe 11 to the object O, the transmitted ultrasonic beam is sequentially reflected on each discontinuous plane of acoustic impedance in each body tissue of the object O and each reflected wave is received as an echo signal by the plural ultrasonic transducers. Amplitude of the received echo signal depends on difference in acoustic impedance between both sides of the discontinuous plane on which the ultrasonic beam is reflected. When a transmitted ultrasonic pulse is reflected by a mobile object such as a flowing blood and a cardiac wall, the echo signal is subjected to frequency shift by the Doppler Effect depending on a velocity component of a mobile object with respect to the transmission direction of the ultrasonic pulse. In the following description, it is assumed that velocity indicates a vector and speed indicates magnitude of a velocity vector (i.e., scalar).

As to the ultrasonic probe 11 of the present embodiment, it is enough that the ultrasonic probe 11 can image an arbitrary cross-section of the object O and can image the object O at a predetermined frame rate while being moved. In other words, the ultrasonic probe 11 is not limited to a specific type such as a convex type, and arrangement of the ultrasonic transducers inside the ultrasonic probe 11 is not limited to specific arrangement.

The positional-information acquisition device 12 can be configured of, for example, a magnetic sensor, an infrared sensor, an optical sensor, or a velocity sensor. Additionally, when a housing (or holder) of the ultrasonic probe 11 is provided with a marker, the positional-information acquisition device 12 may compute positional information of the ultrasonic probe 11 on the basis of images of this marker which are imaged from plural directions by respective cameras. In this case, it is preferable that distance between the marker and a predetermined position of the housing of the ultrasonic probe 11 or between the marker and an arrangement plane of the ultrasonic transducers is preliminarily stored as offset information in memory circuitry 56.

Hereinafter, a description will be given of a case where the positional-information acquisition device 12 includes a transmitter, a magnetic sensor as a positional sensor, and a control device and is connected to the processing circuitry 57 via an interface circuit 55.

In this case, the transmitter of the positional-information acquisition device 12 transmits a reference signal. Specifically, the transmitter is disposed at an arbitrary position, and forms a magnetic field which is centered on the position of the transmitter and is directed outward. The magnetic sensor as a positional sensor acquires positional information in three-dimensional space by receiving the reference signal. Specifically, the magnetic sensor as a positional sensor is provided on the surface of the ultrasonic probe 11, detects the three-dimensional magnetic field formed by the transmitter, converts the detected magnetic field into an information signal, and outputs the information signal to the control device of the positional-information acquisition device 12.

In this case, the control device calculates coordinates and orientation of the magnetic sensor in a three-dimensional coordinate system, the origin of which is the position of the transmitter, on the basis of the information signal received from the magnetic sensor, and outputs the obtained coordinates and orientation as positional information of the ultrasonic probe 11 to the processing circuitry 57. It is preferable that the object O is positioned within a range in which the magnetic sensor attached to the ultrasonic probe 11 can accurately detect the output magnetic field of the transmitter.

The input circuit 20 is configured as, for example, an operation panel, and includes a touch panel and a hardware key. The touch panel functions as a touch command screen, and includes a display and a touch input circuit provided adjacent to this display. The display of the touch panel is configured of a general display output device such as a liquid crystal display and an OLED (Organic Light Emitting Diode) display. The touch input circuit provides the main body 40 with indicated-position information on the touch input circuit instructed by a user. The hardware key is, for example, a keyboard, a mouse, a foot switch, a track ball, and/or various types of buttons.

The input circuit 20 receives various types of instructions from a user of the ultrasonic diagnostic apparatus 10, and transfers the received instructions to the main body 40 via the interface circuit 55. Specifically, the touch input circuit and the hardware key receive, for example, a positioning start instruction and/or a positioning completion instruction from a user, and output an operational input signal corresponding to the operation of the user to the main body 40.

The display 30 is configured of a general display output device such as a liquid crystal display and an OLED display, and displays ultrasonic images generated by the main body 40. Additionally, the display 30 displays, for example, an image for a user of the ultrasonic diagnostic apparatus 10 to input various types of instructions with the use of the input circuit 20.

The main body 40 generates volume data from, for example, echo data which are acquired on the basis of echo signals received by the ultrasonic probe 11 from the object O.

Additionally, the main body 40 generates from the volume data ultrasonic images such as an MPR (Multi Planar Reconstruction) image, a volume rendering image, and a surface rendering image, and causes the display 30 to display the generated ultrasonic images.

As shown in FIG. 1, the main body 40 includes a transmission/reception circuit 50, a B-mode processing circuit 51, a Doppler processing circuit 52, an image generation circuit 53, an image memory 54, the above-described interface circuit 55, the above-described memory circuitry 56, and the above-described processing circuitry 57.

The transmission/reception circuit 50 includes a transmitting circuit 50a and a receiving circuit 50b. The transmission/reception circuit 50 causes the ultrasonic probe 11 to transmit ultrasonic waves toward the object O and generates echo data on the basis of the echo signals received by the ultrasonic probe 11 by controlling transmission directivity and reception directivity in transmission and reception of ultrasonic waves.

The transmitting circuit 50a includes circuit elements such as a pulse generator, a transmission delay circuit, and a pulsar circuit, and supplies the ultrasonic probe 11 with a driving signal. The pulse generator repeatedly generates a rate pulse for forming a transmission ultrasonic wave at a predetermined rate frequency. The transmission delay circuit provides each rate pulse generated by the pulse generator with a delay time, which is separately determined for each ultrasonic transducer and is necessary for converging ultrasonic waves generated by the ultrasonic probe 11 into an ultrasonic beam and determining transmission directivity. Additionally, the pulsar circuit applies a driving pulse to the ultrasonic probe 11 at timing on the basis of each rate pulse. The transmission delay circuit appropriately adjusts a transmission direction of an ultrasonic beam transmitted from the ultrasonic transducer plane by changing the delay time provided to each rate pulse.

Further, in order to execute a predetermined scan sequence under the control of the processing circuitry 57, the transmitting circuit 50a has a function of instantaneously changing parameters such as a transmission frequency and a transmission driving voltage. The function of changing a transmission driving voltage is implemented by a structure of electrically switching plural power-supply units or implemented by a linear-amplifier type of oscillator which is capable of instantaneously changing the value of the transmission driving voltage.

The receiving circuit 50b includes circuit elements such as an amplifier circuit, an A/D converter, and an adder circuit. The receiving circuit 50b receives echo signals received by the ultrasonic probe 11, and generates echo data by performing various types of processing on the echo signals. The amplifier circuit performs gain correction processing on the echo signals by amplifying the echo signals for each channel. The A/D converter performs A/D conversion on the echo signals subjected to the gain correction processing, and provides the digitized data of the echo signals with each delay time necessary for determining reception directivity. The adder circuit performs addition processing of the echo signals digitized by the A/D converter so as to generate echo data. The addition processing performed by the adder circuit enhances each reflected component from a direction in accordance with reception directivity of each echo signal.

In the present embodiment, the transmitting circuit 50a can cause the ultrasonic probe 11 to transmit a two-dimensional ultrasonic beam toward the object O. Additionally, the receiving circuit 50b can generate two-dimensional echo data from echo signals received by the ultrasonic probe 11. Further, the processing circuitry 57 generates volume data based on plural two-dimensional echo data, which have been acquired at a predetermined frame rate while the ultrasonic probe 11 is being moved, and also based on positional information of the ultrasonic probe 11 at the acquisition time of each of the plural two-dimensional echo data.

The B-mode processing circuit 51 receives the echo data from the receiving circuit 50b and performs predetermined processing such as logarithmic amplification and envelope detection on the echo data so as to generate B-mode data in which signal intensity is indicated by brightness.

The Doppler processing circuit 52 performs frequency analysis on velocity information included in the echo data received from the receiving circuit 50b, and extracts a blood-flow component, a tissue component, and a contrast-agent echo component by the Doppler Effect. In this manner, the Doppler processing circuit 52 generates Doppler data in which moving-object information items such as average velocity, variance, and power are extracted for multiple points.

The image generation circuit 53 generates ultrasonic image data based on echo signals received by the ultrasonic probe 11. For instance, the image generation circuit 53 generates two-dimensional B-mode image data, in which intensity of a reflected wave is indicated by brightness, from two-dimensional B-mode data generated by the B-mode processing circuit 51. Additionally, the image generation circuit 53 generates image data of a two-dimensional color Doppler image indicative of moving-object information from two-dimensional Doppler data generated by the Doppler processing circuit 52 in such a manner that the two-dimensional color Doppler image is generated as an average velocity image, a variance image, a power image, or a combination image of these images.

The image memory 54 is a memory circuit configured to store data of two-dimensional ultrasonic images generated by the processing circuitry 57.

The interface circuit 55 is an interface configured to control transmission/reception of data between the positional-information acquisition device 12, the network 100, the external device 101 such as a modality and an image server, and the processing circuitry 57. For instance, the positional-information acquisition device 12 acquires positional information of the ultrasonic probe 11, and outputs the acquired positional information to the processing circuitry 57 via the interface circuit 55.

The memory circuitry 56 is equipped with a configuration including memory media which can be read by a processor such as a magnetic memory medium, an optical memory medium, and a semiconductor memory. The memory circuitry 56 may be configured such that some or all of the programs and data stored in those memory media can be downloaded by means of communication via an electronic network. The memory circuitry 56 stores volume data generated by the processing circuitry 57 for example. Additionally, the memory circuitry 56 may store volume data acquired from the external device 101 via the network 100.

The processing circuitry 57 is a processor, which implements a function of controlling the entirety of the ultrasonic diagnostic apparatus 10 and performs processing of assisting a user in acquiring satisfactory volume data regardless of skills of the user by reading out and executing a medical image processing program stored in the memory circuitry 56. This assistance processing may be performed in real time while the ultrasonic probe 11 is being moved or may be performed at the time of reviewing images after completion of a scan.

Figure 2:
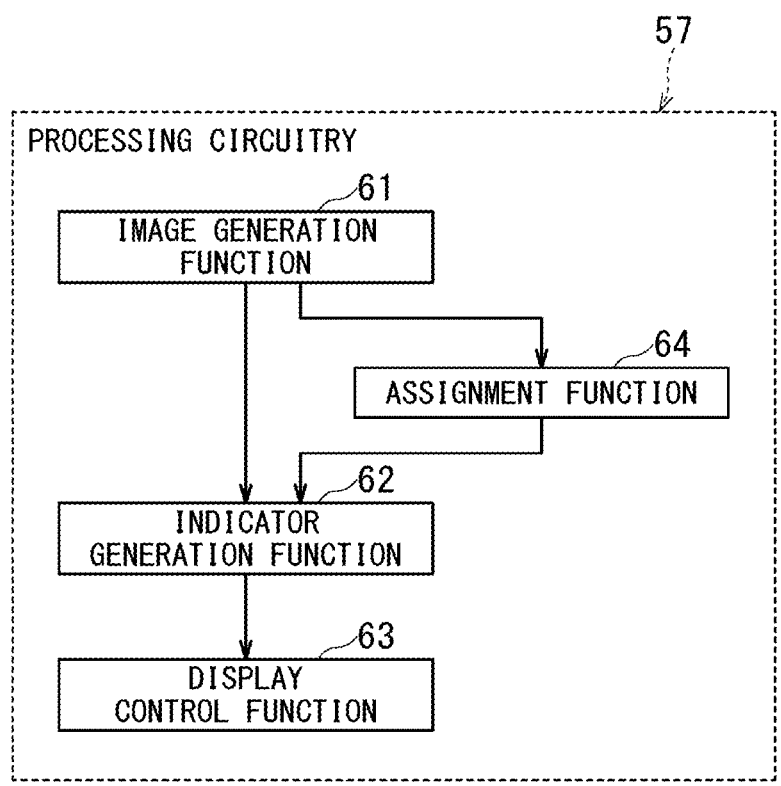
FIG. 2 is a schematic block diagram illustrating an example of functions implemented by a processor of a processing circuitry.

FIG. 2 is a schematic block diagram illustrating functions implemented by the processor of the processing circuitry 57. As shown in FIG. 2, the processor of the processing circuitry 57 implements an image generation function 61, an indicator generation function 62, a display control function 63, and an assignment function 64. These functions 61 to 64 are stored in the form of programs in the memory circuitry 56. Note that the assignment function 64 may be omitted.

The image generation function 61 generates ultrasonic images for display such as an MPR image and a rendering image (e.g., a volume rendering image and a surface rendering image) from volume data, the volume data being generated on the basis of echo data acquired by moving the ultrasonic probe 11 and output data from the magnetic sensor provided as a positional sensor on the ultrasonic probe 11. The ultrasonic images for display include at least one cross-sectional image corresponding to one cross-section for example.

Specifically, the image generation function 61 associates B-mode data with positional information, which indicates three-dimensional position of the ultrasonic probe 11 at the time of receiving original echo signals of these B-mode data from the object O and is acquired from the positional-information acquisition device 12. Additionally, the image generation function 61 generates volume data (i.e., three-dimensional ultrasonic image data) on the basis of plural time-sequential B-mode data to be acquired in series and the positional information associated with each of the B-mode data. Further, the image generation function 61 generates ultrasonic images for display (hereinafter, referred to as display ultrasonic images) from the volume data.

The indicator generation function 62 generates a support image (hereinafter, referred to as an indicator) for assisting a user in acquiring satisfactory volume data regardless of skills of the user.

The indicator generation function 62 generates an indicator which indicates, for example, speed of the ultrasonic probe 11 obtained on the basis of output from the positional sensor and a recommended speed range of moving the ultrasonic probe 11 (hereinafter, referred to as "the first indicator").

Additionally, the indicator generation function 62 generates an indicator which indicates distribution of echo-data acquisition density in at least one cross-section obtained on the basis of output of the positional sensor (hereinafter, referred to as "the second indicator").

Further, when the processing circuitry 57 implements the assignment function 64, the indicator generation function 62 generates an indicator which is based on information indicative of uniformity of acquisition density assigned by the assignment function 64 with respect to the voxels corresponding to at least one cross-section of volume data (hereinafter, referred to as "the third indicator").

The display control function 63 causes the display 30 to display one or plural display ultrasonic images generated by the image generation function 61 and indicators generated by the indicator generation function 62.

The assignment function 64 calculates echo-data acquisition density of each voxel of volume data on the basis of output of the positional sensor.

First Indicator

Next, a description will be given of display processing for displaying the first indicator, which indicates speed of the ultrasonic probe 11 obtained on the basis of output of the positional sensor and a recommended speed range of moving the ultrasonic probe 11.

Figure 3A:
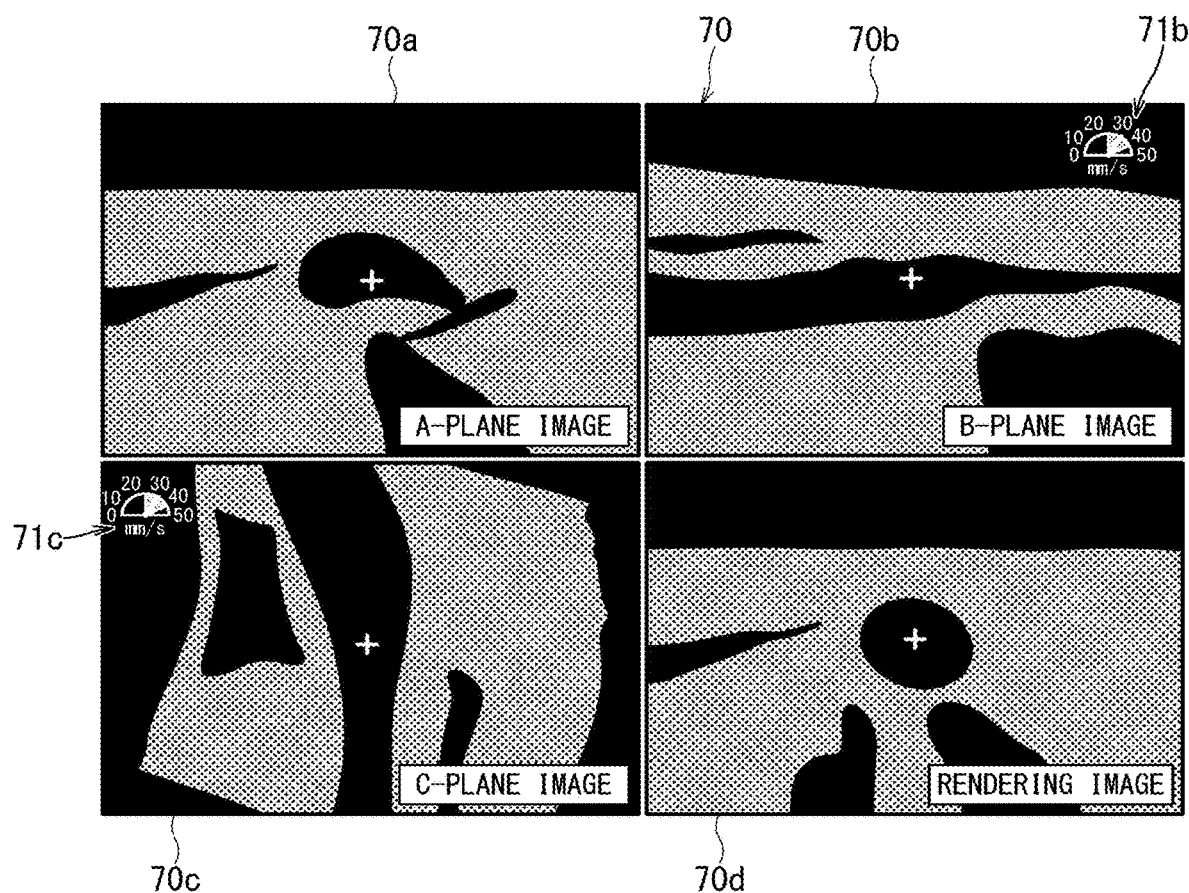
FIG. 3A is a schematic diagram illustrating a screen in which a display ultrasonic image and the first indicator are displayed.
Figure 3B:
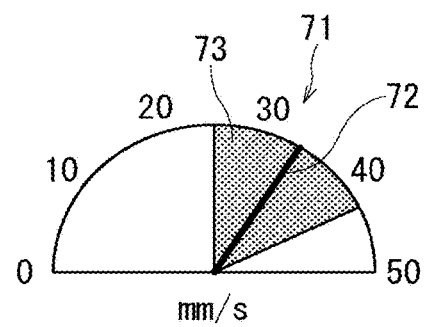
FIG. 3B is an enlarged schematic diagram showing one example of the first indicator.

FIG. 3A is a schematic diagram illustrating a screen in which a display ultrasonic image 70 and the first indicator 71*b* and 71*c* are displayed, and FIG. 3B is an enlarged schematic diagram showing one example of the first indicator 71.

As shown in FIG. 3A, the display control function 63 can cause the display 30 to display plural display ultrasonic images, which are generated by the image generation function 61, in parallel. FIG. 3A illustrates a case where a rendering image 70*d* and three orthogonal cross-sectional images including an A-plane image 70*a*, a B-plane image 70*b*, and a C-plane image 70*c* are displayed as plural display ultrasonic images. As to cross-sectional images, there is not substantial difference between a cross-sectional image on the basis of volume data obtained from a convex scan and a cross-sectional image on the basis of volume data obtained from a linear scan. Additionally, volume data to be generated by the processing circuitry 57 are not limited to volume data generated under the B-mode but may be generated under the color Doppler mode or the elastography imaging mode.

Further, as shown in FIG. 3A and FIG. 3B, the indicator generation function 62 generates the first indicator 71 for each cross-sectional image in such a manner that the first indicator 71 indicates in-plane speed 72 of the ultrasonic probe 11 within each cross-section obtained on the basis of output of the positional sensor and indicates a recommended range 73 of speed for moving ultrasonic probe in each plane. The display control function 63 composes each cross-sectional image with the first indicator 71 corresponding to this cross-sectional image so as to generate a composite image, and causes the display 30 to display the composite image.

FIG. 3A illustrates a case where the first indicator 71*b* corresponding to the B-plane image 70*b* is composed with the B-plane image 70*b* so as to be displayed as a composite image and the first indicator 71*c* corresponding to the C-plane image 70*c* is composed with the C-plane image 70*c* so as to be displayed as a composite image. When the A-plane matches the scanning plane and the ultrasonic probe 11 is moved in the direction perpendicular to the A-plane, the in-plane component of the velocity of the ultrasonic probe 11 within the A-plane can be regarded as approximately zero and thus the first indicator 71*a* corresponding to the A-plane image 70*a* may be omitted (FIG. 3A).

Information on the recommended range 73 may be inputted by a user via the input circuit 20 or may be previously stored in the memory circuitry 56. When the information on the recommended range 73 is previously stored in the memory circuitry 56, the information on the recommended range 73 may be associated with scan conditions for acquiring echo data and the type of the ultrasonic probe 11. For instance, when it is desirable to display an imaging target part included in the scan conditions as an image with higher resolution, i.e., when volume data with higher data density are desirable for an imaging target part included in the scan conditions, it is desirable that the recommended range 73 of speed is set to a lower range.

For instance, the recommended range 73 of speed for moving the ultrasonic probe 11 is determined depending on a frame rate. Since a frame rate depends on, for example, a scanning range, scanning line density, and number of parallel simultaneous reception, it can be restated that the recommended range 73 is determined depending on those parameters. The higher the frame rate is, the more likely data density is to be kept higher in the case of moving the ultrasonic probe 11 at high speed. Additionally, the recommended range 73 is determined depending on, for example, a target part (i.e., anatomical imaging target part) for which echo data are acquired. Depending on a target part, slice thickness (i.e., thickness of an ultrasonic beam) is set to a small value in order to image a small observation target in some cases. This is because the smaller the slice thickness is, the more likely it is to obtain an image with high resolution.

However, when the ultrasonic probe 11 is moved at high speed under the state where the slice thickness is thin, there is a possibility that a scan is performed under the state where a small observation target is not included in the slice (i.e., not included in the irradiation range of the ultrasonic beam). In other words, a risk of missing (i.e., failing to image) a small observation target is increased. Thus, in the case of scanning a target which requires thinner slice thickness, it is preferable that the recommended range 73 is set as a range of lower speed.

Additionally, it is sufficient that the first indicator 71 indicates speed 72 of the ultrasonic probe 11 and the recommended range 73 of speed, and the first indicator 71 is not limited to those shown in FIG. 3A and FIG. 3B. For instance, the indicator generation function 62 may generate a colored frame of each cross-sectional image as the first indicator 71. The colored frame and the first indicator 71 shown in FIG. 3A and FIG. 3B. can be used alternatively or in combination.

When a colored frame of each cross-sectional image is generated as the first indicator 71, the indicator generation function 62 changes color of the frame of each cross-sectional image depending on, for example, the speed 72 of the ultrasonic probe 11 within each plane. In this case, the indicator generation function 62 determines color of the frame of each cross-sectional image on the basis of, for example, a color map or a gray-scale map.

Further, when a colored frame of each cross-sectional image is generated as the first indicator 71, the indicator generation function 62 may change color of the frame of each cross-sectional image depending on relationship between the speed 72 of the ultrasonic probe 11 within each plane and the recommended range 73 of speed for moving the ultrasonic probe 11. Specifically, when the speed 72 of the ultrasonic probe 11 within each plane exceeds the recommended range 73, the indicator generation function 62 can color the frame of the corresponding cross-sectional image with red so as to intuitively warn a user that the speed 72 of the ultrasonic probe 11 within each plane has exceeded the recommended range 73.

Next, a description will be given of definitions the A-plane, the B-plane, and the C-plane shown in FIG. 3A.

Figure 4A:
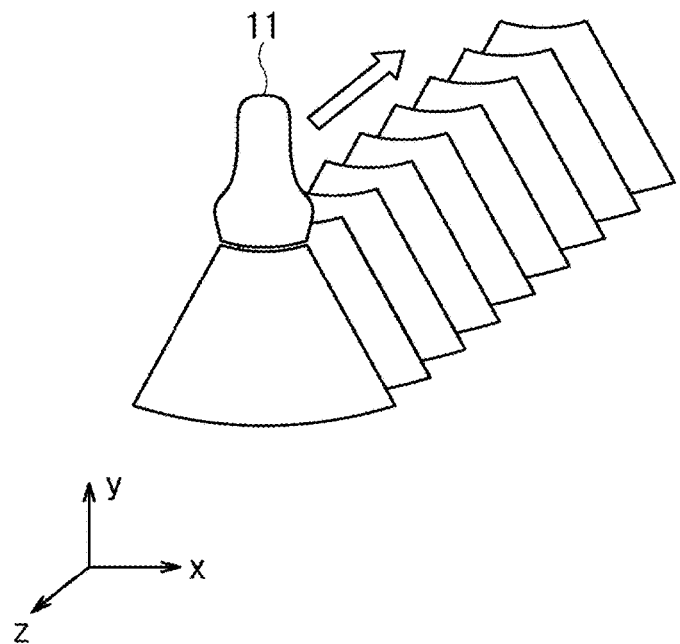
FIG. 4A is a schematic diagram illustrating a case where the ultrasonic probe is linearly moved in the direction perpendicular to the scanning plane.
Figure 4B:
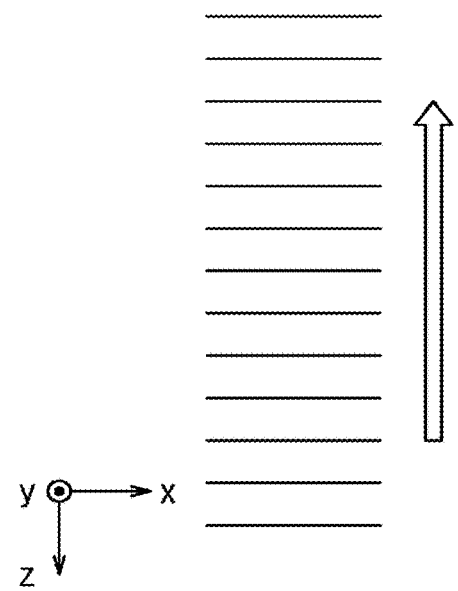
FIG. 4B is a z-x plan view when
Figure 4C:
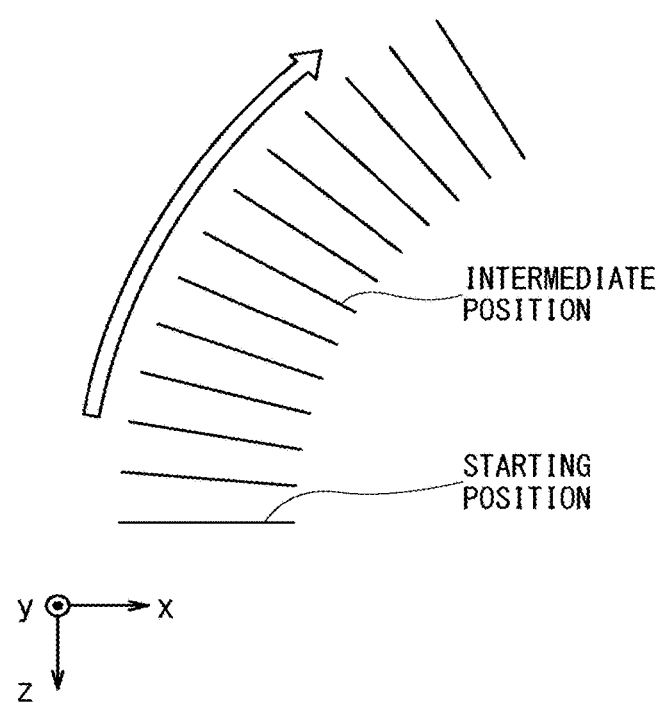
FIG. 4C is a z-x plan view in the case of moving the ultrasonic probe in a curved path.
Figure 4C:
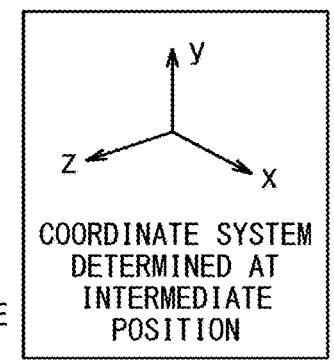
Figure 4C:
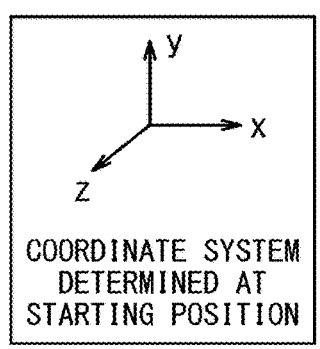

FIG. 4A is a schematic diagram illustrating a case where the ultrasonic probe 11 is linearly moved in the direction perpendicular to the scanning plane, FIG. 4B is a z-x plan view when FIG. 4A is viewed in the direction of the y-axis, and FIG. 4C is a z-x plan view in the case of moving the ultrasonic probe 11 in a curved path.

The three orthogonal coordinate axes shown as an example in FIG. 4A and FIG. 4B are the coordinate axes under the premise that the x-y plane is the scanning plane of the ultrasonic probe 11. When the A-plane, the B-plane, and the C-plane are defined as three cross-sections perpendicular to each other, the positional relationship between the scanning plane, the A-plane, the B-plane, and the C-plane does not change during movement of the ultrasonic probe 11 in the case of linearly moving the ultrasonic probe 11 in the direction perpendicular to the scanning plane. Thus, for instance, when the fixed coordinate system is used by defining the scanning plane at the starting position of the ultrasonic probe 11 as its x-y plane as shown in FIG. 4A and FIG. 4B and the A-plane, the B-plane, and the C-plane are respectively defined as the x-y plane, the y-z plane, and the z-x plane of this fixed coordinate system, the A-plane (i.e., x-y plane) is kept parallel with the scanning plane during movement of the ultrasonic probe 11. In this case, the A-plane image 70a, which is generated from volume data to be generated each time of acquisition of echo data on a real-time basis while the ultrasonic probe 11 is being moved, is always parallel with the scanning plane.

Contrastively, when the ultrasonic probe 11 is moved in a curved path as shown in FIG. 4C, even in the case of using such a coordinate system that the scanning plane at the starting position of the ultrasonic probe 11 is defined as the x-y plane (lower left and lower right in FIG. 4C), the x-y plane of this coordinate system cannot always be parallel with the scanning plane during movement of the ultrasonic probe 11. The same applies to the case of using such a coordinate system that the scanning plane at the intermediate position of the ultrasonic probe 11 is defined as the x-y plane (upper right of FIG. 4C).

Thus, it is preferable to define the A-plane, the B-plane, and the C-plane in consideration of the case where the ultrasonic probe 11 is moved in a curved path.

Figures 5A, 5B, 6:
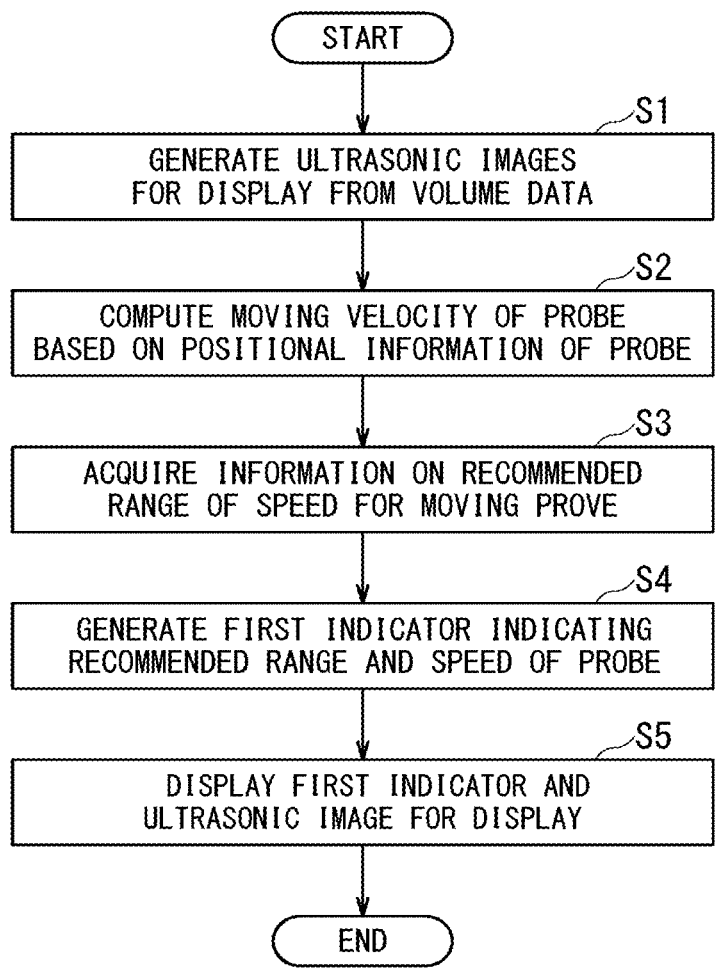
FIG. 5A is a schematic diagram illustrating the first definition method for the A-plane, the B-plane, and the C-plane.
FIG. 5B is a schematic diagram illustrating the second definition method for the A-plane, the B-plane, and the C-plane.
FIG. 6 is a flowchart illustrating the processing of displaying the first indicator in which the processing circuitry shown in FIG. 1 assists a user in acquiring satisfactory volume data regardless of skills of the user.

FIG. 5A is a schematic diagram illustrating the first definition method for the A-plane, the B-plane, and the C-plane. FIG. 5B is a schematic diagram illustrating the second definition method for the A-plane, the B-plane, and the C-plane.

The first definition method is such a method that an x-y plane, a y-z plane, and a z-x plane of a predetermined fixed coordinate system are respectively defined as the A-plane, the B-plane, and the C-plane. In this case, it is preferable to use such a coordinate system for a fixed coordinate system that the scanning plane at the starting position of the ultrasonic probe 11 is defined as the x-y plane (lower left and lower right of FIG. 4C). Also in this case, it is preferable to use such a coordinate system for a fixed coordinate system that the scanning plane at the intermediate position of the ultrasonic probe 11 is defined as the x-y plane (upper right of FIG. 4C). For instance, when the processing circuitry 57 performs assistance processing in real time, it is preferable to use the coordinate system in which the scanning plane at the starting position of the ultrasonic probe 11 is defined as the x-y plane.

Additionally, as shown as the second definition method in FIG. 5B, the y-z plane and the z-x plane of the predetermined fixed coordinate system may be respectively defined as the B-plane and the C-plane while the A-plane is being sequentially updated so as to match the scanning plane in real time or in accordance with moving-image reproduction timing at the time of reviewing the images. In this case, though the A-plane is not necessarily orthogonal to the B-plane, the B-mode image itself generated from the acquired two-dimensional B-mode image data can be displayed as the A-plane image 70a.

FIG. 6 is a flowchart illustrating the processing of displaying the first indicator 71 in which the processing circuitry 57 shown in FIG. 1 assists a user in acquiring satisfactory volume data regardless of skills of the user. In FIG. 6, each reference sign composed of S and number on its right side indicates step number of the flowchart.

The processing may be performed in real time or may be performed at the time of reviewing images after completion of imaging. In the following, a description will be given of a case where the processing is performed in real time. In the case of performing the processing in real time, the processing is started when continuous imaging is started at a predetermined frame rate after completing input of scan conditions via the input circuit 20 by a user and starting movement of the ultrasonic probe 11.

First, in the step S1, the image generation function 61 generates display ultrasonic images 70 from volume data, which are generated on the basis of output of the magnetic sensor provided as the positional sensor on the ultrasonic probe 11 and echo data to be acquired while the ultrasonic probe 11 is being moved.

In the next step S2, the indicator generation function 62 calculates positional information of the ultrasonic probe 11 on the basis of output of the positional sensor acquired from the positional-information acquisition device 12, and calculates moving velocity of the ultrasonic probe 11 on the basis of this positional information. In this case, when the display ultrasonic images 70 include one or plural cross-sectional images, the indicator generation function 62 calculates magnitude of the velocity component (i.e., speed 72) within each cross-section.

When the ultrasonic probe 11 moves in a curved path as shown in FIG. 4C, even within the same cross-section, speed of the ultrasonic probe 11 may be different for each position within this cross-section. In this case, speed of the ultrasonic probe 11 at a predetermined position within this cross-section may be represented as the speed of the ultrasonic probe 11 within this cross-section. Also in this case, the average speed of the ultrasonic probe 11 in a part or the entirety of this cross-section may be represented as the speed of the ultrasonic probe 11 within this cross-section.

In the next step S3, the indicator generation function 62 acquires information on the recommended range 73.

In the next step S4, the indicator generation function 62 generates the first indicator 71 indicative of the recommended range 73 and speed 72 of the ultrasonic probe 11. When the display ultrasonic images 70 include one or plural cross-sectional images, the indicator generation function 62 generates the first indicator 71 for each cross-section.

In the next step S5, the display control function 63 composes each display ultrasonic image 70 and the corresponding first indicator 71 so as to generate a composite image, and causes the display 30 to display the composite image (FIG. 3A).

By displaying the first indicator 71 in the above-described manner, it is possible to assist a user in acquiring satisfactory volume data regardless of skills of the user.

When respective images of arbitrary cross-sections are generated from volume data, image quality of those cross-sectional images depend on data density within each of those cross-sections in the volume data. This data density of the volume data depends on moving velocity of the ultrasonic probe 11.

According to the medical image processing apparatus 1 of the present embodiment, a user can easily move the ultrasonic probe 11 within the speed range recommended with respect to each cross-sectional image by, for example, confirming the first indicator 71 displayed in real time, and thus the user can easily acquire satisfactory volume data. Hence, each of display ultrasonic images 70 generated from such volume data has satisfactory image quality, and thus it is possible to improve diagnostic accuracy.

Additionally, when display ultrasonic images 70 are reproduced as a moving image or still images at the time of reviewing those images after completion of imaging, it is possible to easily determine whether each cross-sectional image has been acquired by moving the ultrasonic probe 11 within the recommended range 73 of speed or not by confirming the first indicator 71 displayed together with those display ultrasonic images 70. Since reliability of the generated images can be objectively determined in the above-described manner according to the medical image processing apparatus 1, diagnostic accuracy can be improved and a user can effectively learn how to move the ultrasonic probe 11 such that satisfactory volume data are acquired.

Second Indicator

Next, a description will be given of processing of displaying the second indicator, which is obtained on the basis of output of the positional sensor and indicates distribution of echo-data acquisition density in at least one cross-section.

Figure 7A:
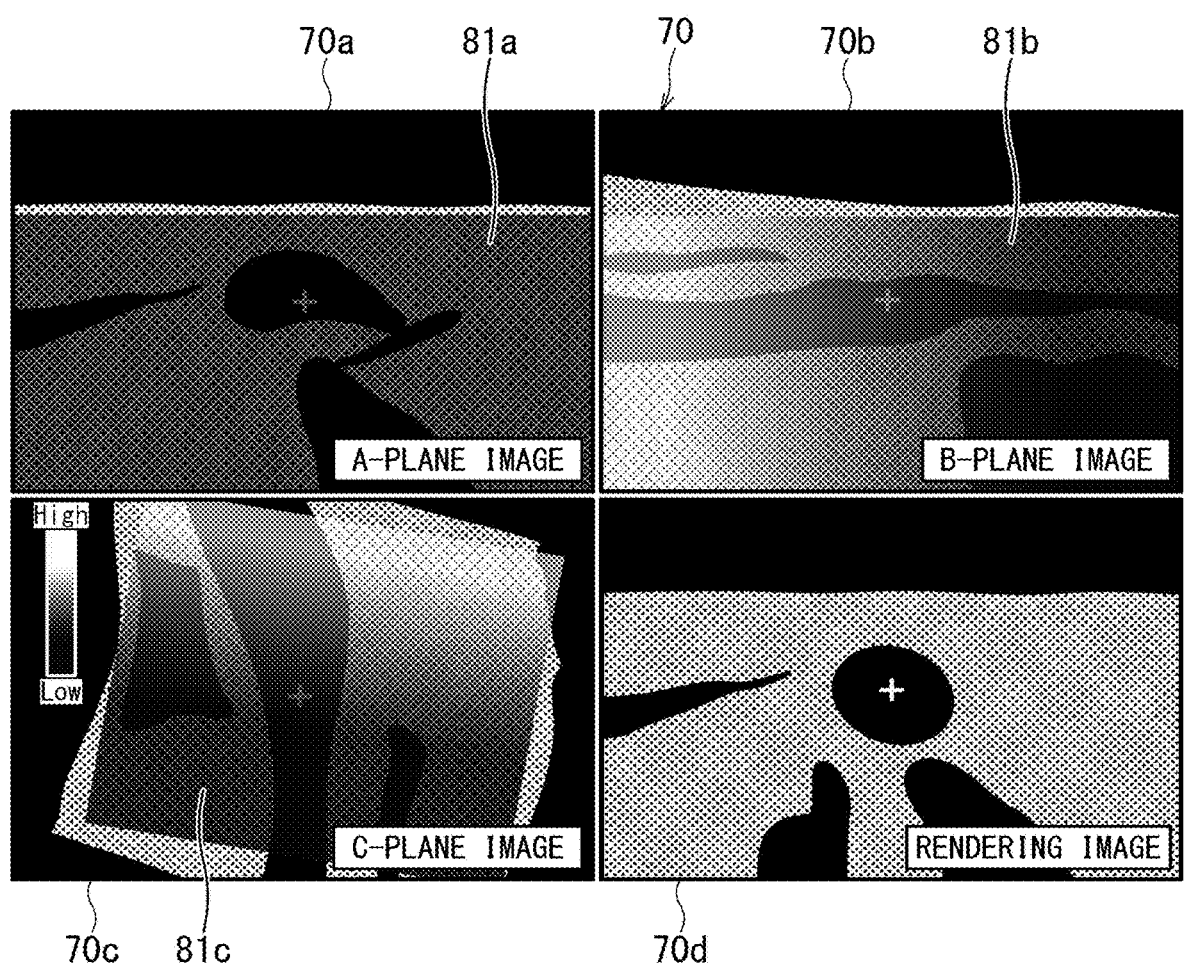
FIG. 7A is a schematic diagram illustrating a case where the second indicators are respectively composed with the display ultrasonic images and the composite images are displayed.
Figure 7B:
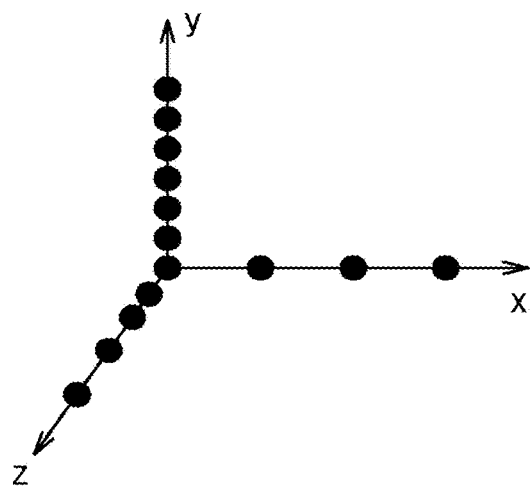
FIG. 7B is a schematic diagram conceptually indicating distribution of echo-data acquisition density.

FIG. 7A is a schematic diagram illustrating a case where the second indicators 81a, 81b, and 81c are respectively composed with the display ultrasonic images 70a, 70b, and 70c and the composite images are displayed. FIG. 7B is a schematic diagram conceptually indicating distribution of echo-data acquisition density.

Each of the second indicators 81a-81c is generated so as to indicate corresponding in-plane density of echo data within the cross-section. For instance, when the scanning plane is parallel with the x-y plane and the moving direction of the ultrasonic probe 11 is parallel with the z-axis direction (FIG. 4A and FIG. 4B), the echo-data acquisition density Dx in the x-axis direction depends on the number of ultrasonic beams in the scanning range. Additionally, the echo-data acquisition density Dy in the y-axis direction depends on the number of samples on each ultrasonic beam. Further, the echo-data acquisition density Dz in the z-axis direction depends on a value obtained by dividing a frame rate by scanning speed of the ultrasonic probe 11. Each of the second indicators 81a to 81c is an image which indicates distribution of echo-data acquisition density by color or by gray-scale on the basis of a color map or a gray-scale map for example.

For instance, in the case of using the first definition method for the A-plane, the B-plane, and the C-plane (FIG. 5A), the second indicator 81a corresponding to the A-plane image 70a indicates echo-data acquisition density within the x-y plane when viewed from the z-axis direction. Similarly, the second indicator 81b corresponding to the B-plane image 70b indicates echo-data acquisition density within the y-z plane when viewed from the x-axis direction, and the second indicator 81c corresponding to the C-plane image 70c indicates echo-data acquisition density within the z-x plane when viewed from the y-axis direction (FIG. 7A and FIG. 7B).

Additionally, it is sufficient that each of the second indicators 81a to 81c indicates in-plane acquisition density of echo data within the corresponding cross-section, and the second indicators 81a to 81c are not limited to those shown in FIG. 7A. For instance, the indicator generation function 62 may generate three colored frames of the respective cross-sectional images as the second indicators 81a to 81c. The colored frames and the second indicators 81a to 81c shown in FIG. 7A may be used alternatively or in combination.

When the colored frames of the respective cross-sectional images are generated as the second indicators 81a to 81c, the indicator generation function 62 changes color of the frame of each cross-sectional image depending on in-plane acquisition density of echo data in each cross-section. In this case, the indicator generation function 62 determines color of the frame of each cross-sectional image on the basis of a color map or a gray-scale map for example.

Figure 8:
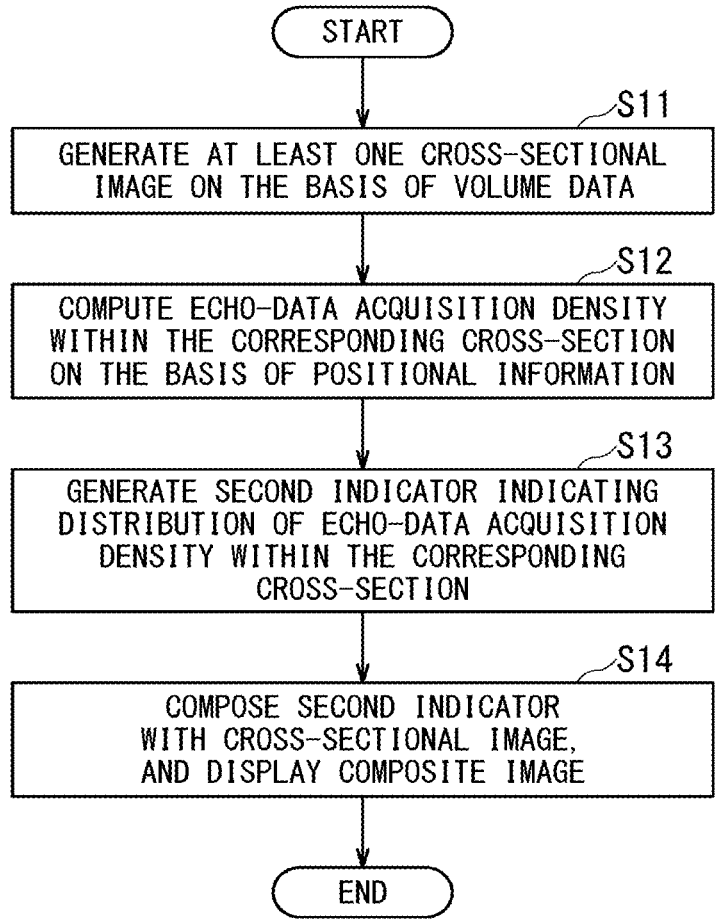
FIG. 8 is a flowchart illustrating processing in which the processing circuitry shown in FIG. 1 assists a user in acquiring satisfactory volume data regardless of skills of the user by causing the display to display the second indicators.

FIG. 8 is a flowchart illustrating processing in which the processing circuitry 57 shown in FIG. 1 assists a user in acquiring satisfactory volume data regardless of skills of the user by causing the display 30 to display the second indicators 81a to 81c. In FIG. 8, each reference sign composed of S and number on its right side indicates step number of the flowchart.

The processing shown in FIG. 8 may be performed in real time or may be performed at the time of reviewing images after completion of imaging. In the following, a description will be given of a case where this processing is performed at the time of reviewing images after completion of imaging.

First, in the step S11, the image generation function 61 generates at least one cross-sectional image 70a, 70b, and/or 70c from volume data, which are generated on the basis of output of the magnetic sensor provided as a positional sensor on the ultrasonic probe 11 and echo data to be acquired while the ultrasonic probe 11 is being moved.

In the next step S12, the indicator generation function 62 calculates echo-data acquisition density for each of the cross-sections, which correspond to the respective cross-sectional images 70a, 70b, and/or 70c generated in the step S11, on the basis of positional information associated with each of the B-mode data.

In the next step S13, the indicator generation function 62 generates the second indicator 81a to 81c, each of which indicates distribution of echo-data acquisition density within the corresponding cross-section.

In the next step S14, the display control function 63 respectively composes the second indicator 81a, 80b, and 81c with the display ultrasonic images 70a, 70b, and 70c so as to generate three composite images, and causes the display 30 to display the three composite images (FIG. 7A).

By displaying the second indicators 81a to 81c in the above-described manner, it is possible to assist a user in acquiring satisfactory volume data regardless of skills of the user.

According to the medical image processing apparatus 1 of the present embodiment, a user can easily keep echo-data acquisition density of each cross-sectional image at appropriate density by, for example, confirming the second indicators 81a to 81c displayed in real time and can easily acquire satisfactory volume data. Hence, each of display ultrasonic images 70 generated from such volume data has satisfactory image quality, and thus it is possible to improve diagnostic accuracy.

Additionally, it is possible to easily recognize echo-data acquisition density of each cross-sectional image by, for example, confirming the second indicators 81a to 81c at the time of reviewing images after completion of imaging. Since reliability of the generated images can be objectively determined in the above-describe manner according to the medical image processing apparatus 1, diagnostic accuracy can be improved and a user can effectively learn how to move the ultrasonic probe 11 such that satisfactory volume data are acquired.

Third Indicator

Next, a description will be given of processing of displaying the third indicator, which is generated on the basis of information indicating uniformity of acquisition density assigned to voxels corresponding to at least one cross-section of volume data.

Figure 9:
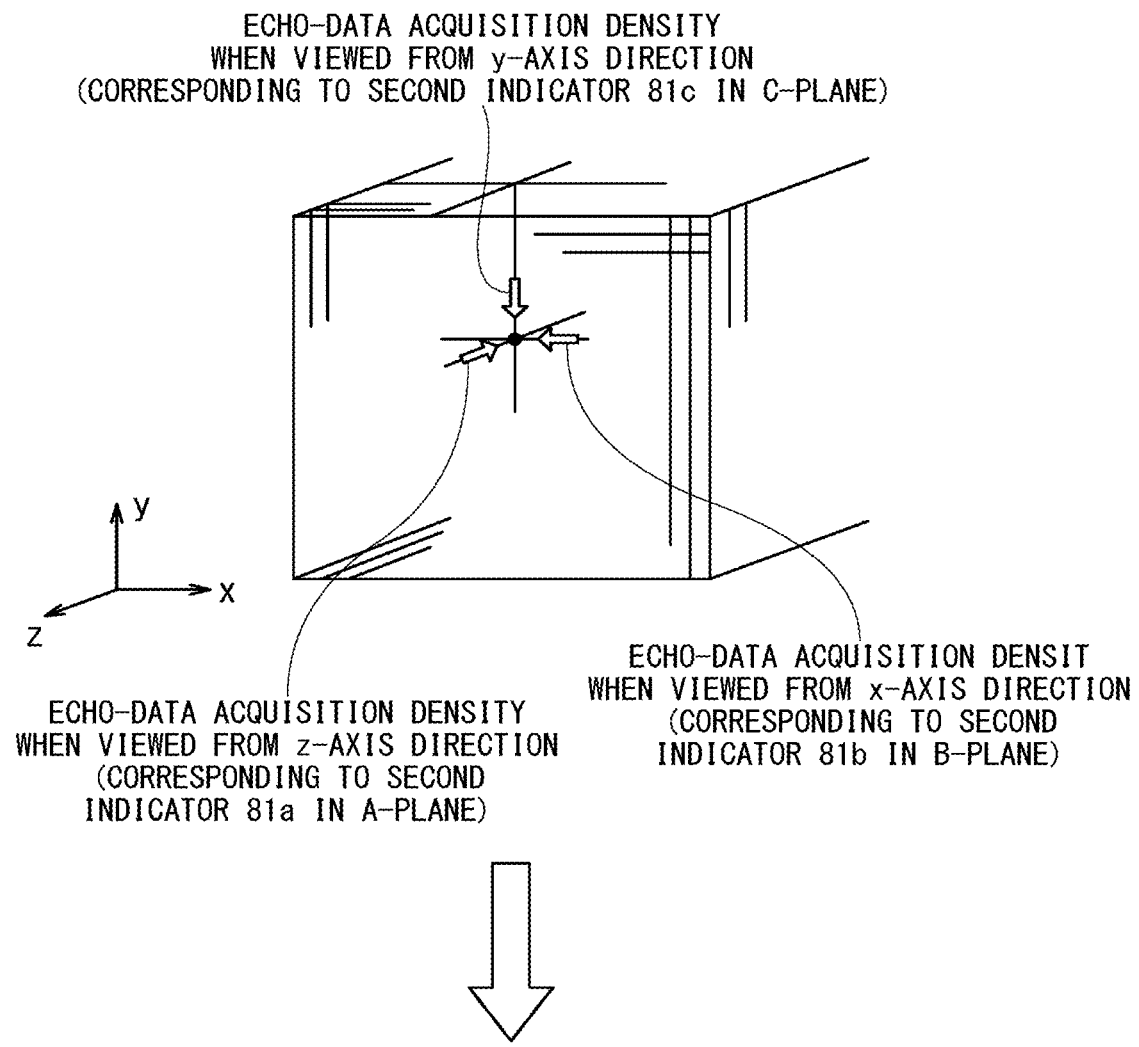
FIG. 9 is a schematic diagram illustrating relationship between the second indicators and the third indicator.

FIG. 9 is a schematic diagram illustrating relationship between the second indicators and the third indicator.

Figure 10:
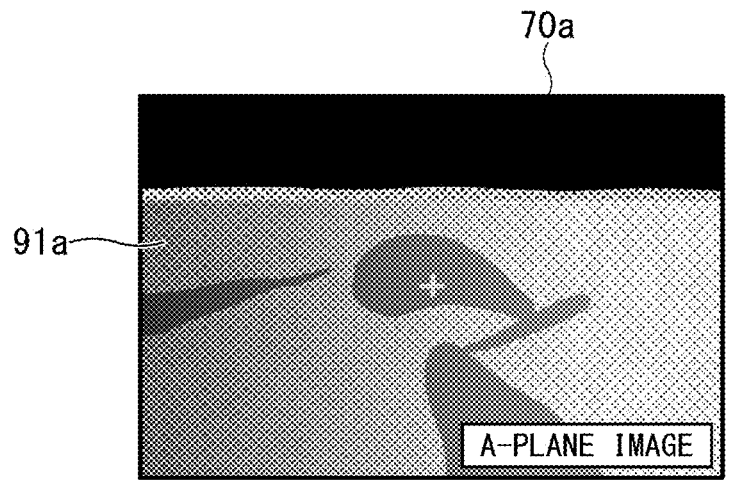
FIG. 10 illustrates a schematic composite image, which is generated by composing the third indicator with the A-plane image to be displayed on the display.

FIG. 10 illustrates a schematic composite image, which is generated by composing the third indicator 91a with the A-plane image 70a to be displayed on the display 30.

The third indicator is generated as an indicator representing uniformity of echo-data acquisition density. Volume data are desirably uniform in data density in every observation direction. However, distribution of echo-data acquisition density indicated by each of the second indicators is different depending on an observation direction. For this reason, the indicator generation function 62 generates the third indicator in such a manner that uniformity of echo-data acquisition density can be confirmed at the time of, for example, reviewing images after completion of imaging.

Specifically, the assignment function 64 assigns information indicating uniformity of data acquisition density to each of voxels constituting volume data. More specifically, the assignment function 64 assigns variance to each voxel of the volume data such that variance assigned to each voxel is obtained from respective axial components of data acquisition density in each voxel. This variance is given by the following equation (1).

$$\sigma^2 = 1/3 * ((Dx - Dave)^2 + (Dy - Dave)^2 + (Dz - Dave)^2) \quad (1)$$

In the equation (1), Dx, Dy, and Dz respectively indicate echo-data acquisition density in the x-axis direction, the y-axis direction, and the z-axis direction, and Dave indicates average of echo-data acquisition density.

The indicator generation function 62 generates the third indicator indicative of distribution of the variance assigned to the voxels corresponding to, for example, a predetermined cross-section. FIG. 10 shows an example of a displayed composite image to be acquired as a result of composing the third indicator 91a with the A-plane image 70a.

Figure 11:
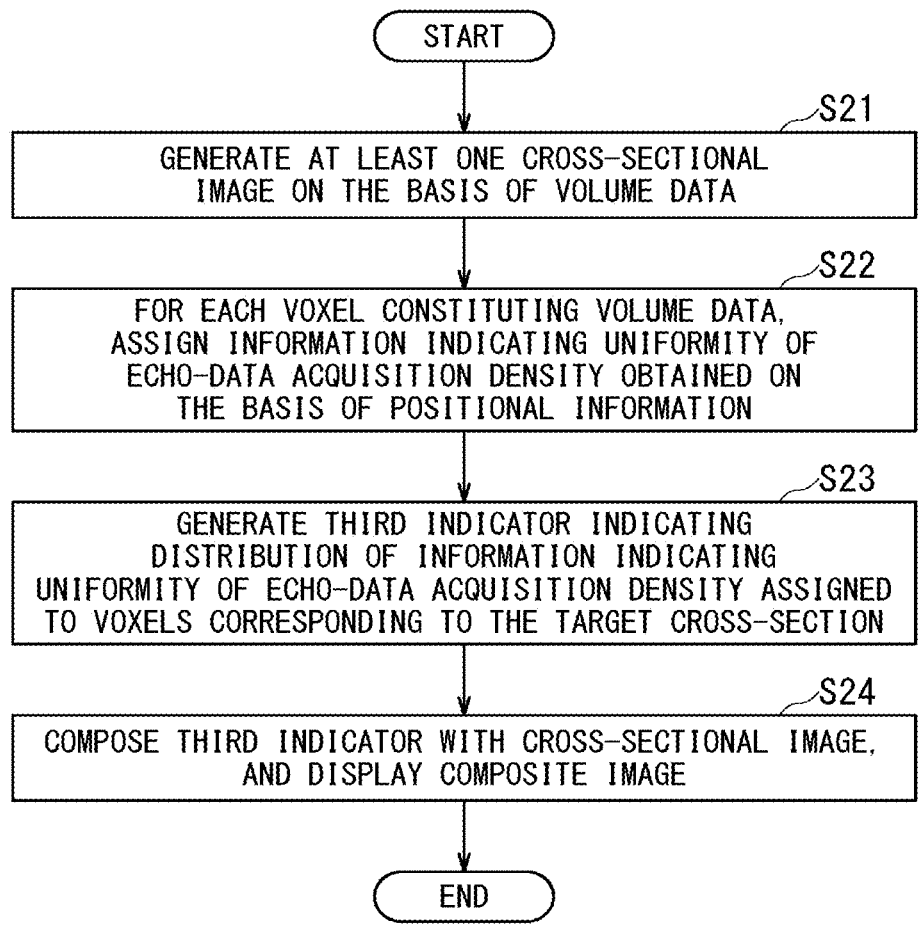
FIG. 11 is a flowchart illustrating processing in which the processing circuitry shown in FIG. 1 assists a user in acquiring satisfactory volume data regardless of skills of the user by causing the display to display the third indicator.

FIG. 11 is a flowchart illustrating processing in which the processing circuitry 57 shown in FIG. 1 assists a user in acquiring satisfactory volume data regardless of skills of the user by causing the display 30 to display the third indicator 91a. In FIG. 11, each reference sign composed of S and number on its right side indicates step number of the flowchart.

The processing shown in FIG. 11 may be performed in real time or may be performed at the time of reviewing images after completion of imaging. In the following, a description will be given of a case where this processing is performed at the time of reviewing images after completion of imaging.

First, in the step S21, the image generation function 61 generates at least one cross-sectional image from volume data, which are generated on the basis of output of the magnetic sensor provided as a positional sensor on the ultrasonic probe 11 and echo data to be acquired while the ultrasonic probe 11 is being moved. In the following, a description will be given of a case where the A-plane image 70a is generated as a cross-sectional image.

In the next step S22, to each voxel constituting the volume data, the assignment function 64 assigns information indicating uniformity of echo-data acquisition density obtained on the basis of output of the positional sensor. Specifically, the assignment function 64 calculates data acquisition density on the basis of positional information associated with each of the B-mode data. Further, the assignment function 64 assigns variance to each voxel of the volume data by using the equation (1) in such a manner that each voxel is assigned with variance obtained from respective axial components of echo-data acquisition density in each voxel.

In the next step S23, the indicator generation function 62 generates the third indicator 91a which indicates the distribution of information (e.g., variance) indicating the uniformity of echo-data acquisition density assigned in the step S22 to the voxels corresponding to the cross-section corresponding to the A-plane image 70a generated in the step S21.

In the next step S24, the display control function 63 composes the third indicator 91a with the A-plane image 70a so as to generate a composite image, and causes the display 30 to display the composite image (FIG. 10).

By displaying the third indicator 91a in the above-described manner, it is possible to assist a user in acquiring satisfactory volume data regardless of skills of the user.

According to the medical image processing apparatus 1 of present embodiment, a user can easily keep satisfactory uniformity of echo-data acquisition density by, for example, confirming the third indicator 91a to be displayed in real time, and easily can acquire satisfactory volume data. Hence, each of display ultrasonic images 70 generated from such volume data has satisfactory image quality, and thus it is possible to improve diagnostic accuracy.

Additionally, it is possible to easily confirm uniformity of echo-data acquisition density by, for example, confirming the third indicator 91a at the time of reviewing ultrasonic images after completion of imaging. Since reliability of the generated images can be objectively determined in the above-described manner according to the medical image processing apparatus 1, diagnostic accuracy can be improved and a user can effectively learn how to move the ultrasonic probe 11 such that satisfactory volume data are acquired.

Second Embodiment

Next, a description will be given of the medical image processing apparatus and the medical image processing method according to the second embodiment.

Figure 12:
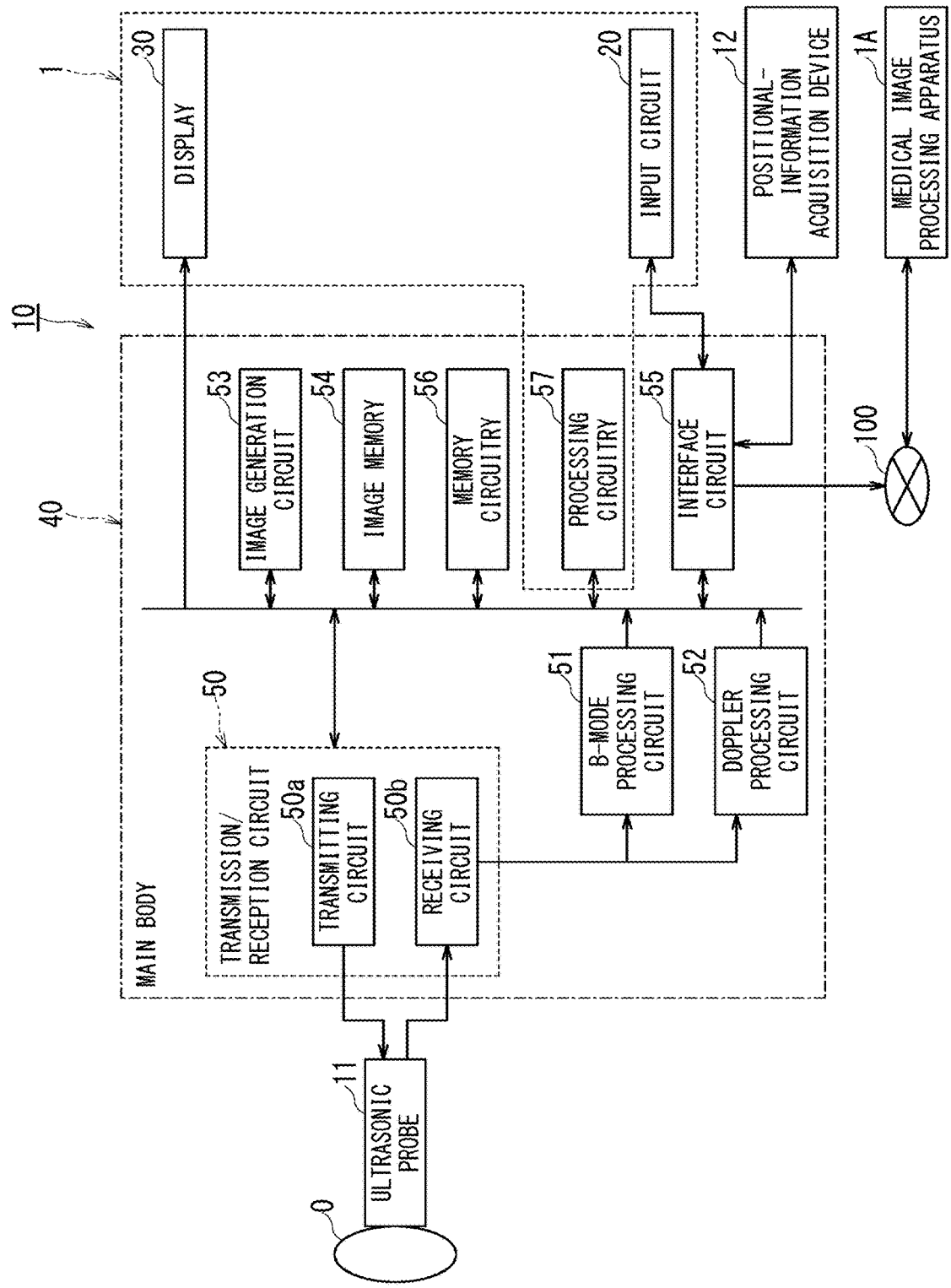
FIG. 12 is a block diagram illustrating configuration of the ultrasonic diagnostic apparatus and the medical image processing apparatus according to the second embodiment.
Figure 13:
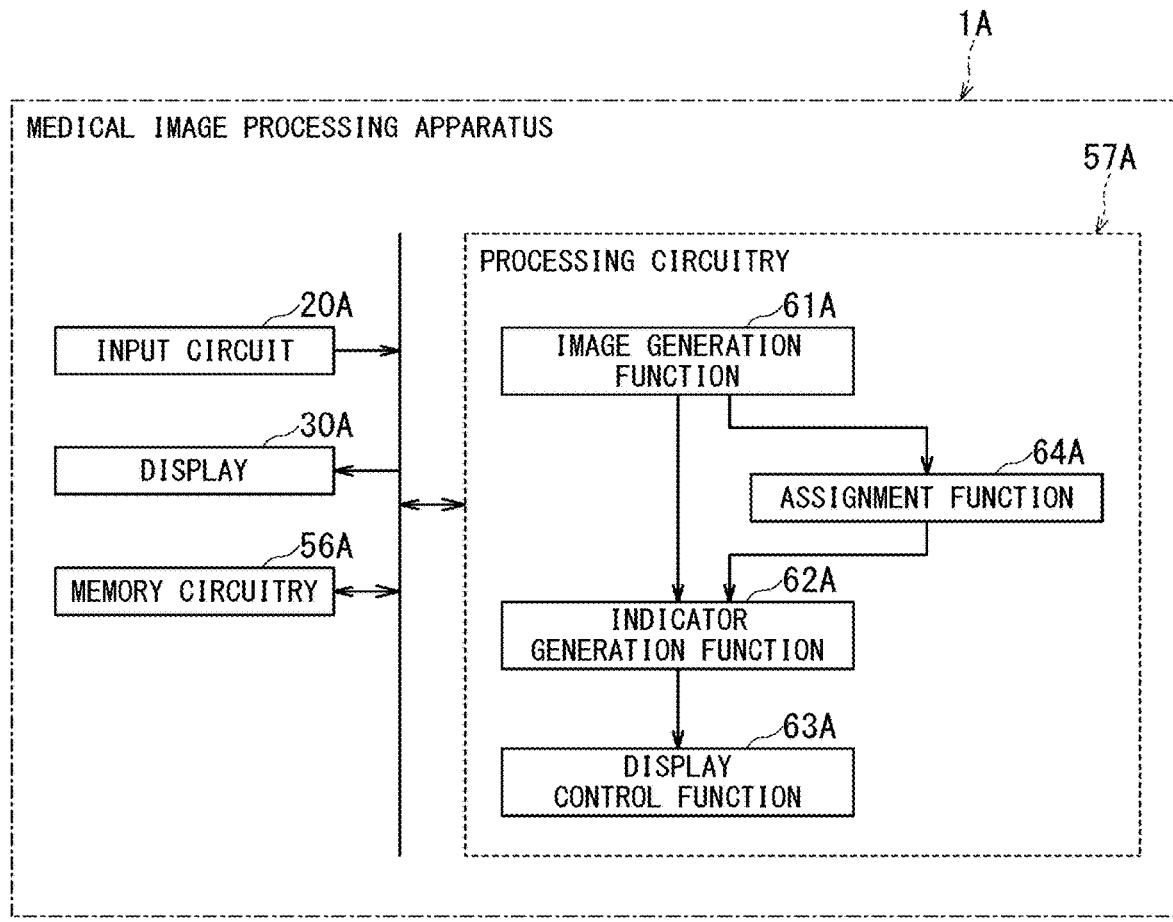
FIG. 13 is a block diagram illustrating internal configuration of the medical image processing apparatus in the second embodiment.

FIG. 12 is a block diagram illustrating configuration of the ultrasonic diagnostic apparatus 10 and the medical image processing apparatus 1A according to the second embodiment. Additionally, FIG. 13 is a block diagram illustrating internal configuration of the medical image processing apparatus 1A in the second embodiment.

The ultrasonic diagnostic apparatus 10 of the second embodiment differs from the ultrasonic diagnostic apparatus 10 of the first embodiment in that the ultrasonic diagnostic apparatus 10 of the second embodiment is provided independently of the medical image processing apparatus LA. Since the other configuration and operations of the ultrasonic diagnostic apparatus 10 in the second embodiment are substantially the same as the ultrasonic diagnostic apparatus 10 shown in FIG. 1, the same reference signs are given for identical components and duplicate description is omitted.

The medical image processing apparatus 1A is provided independently of the ultrasonic diagnostic apparatus 10. For instance, the medical image processing apparatus 1A is connected to the ultrasonic diagnostic apparatus 10 via the network 100 so as to be able to transmit and receive data to/from the ultrasonic diagnostic apparatus 10.

In terms of operation and effect, an input circuit 20A, a display 30A, memory circuitry 56A, and processing circuitry 57A of the medical image processing apparatus 1A respectively function in the same manner as the input circuit 20, the display 30, the memory circuitry 56, and the processing circuitry 57 (of the main body 40) in the first embodiment.

Additionally, the processing circuitry 57A shown in FIG. 13 implements an image generation function 61A, an indicator generation function 62A, a display control function 63A, and an assignment function 64A such that those functions 61A, 62A, 63A, and 64A are respectively equivalent to the image generation function 61, the indicator generation function 62, the display control function 63, and the assignment function 64 in the first embodiment. In other words, the processing circuitry 57A of the medical image processing apparatus 1A receives at least echo data and positional information from the ultrasonic diagnostic apparatus 10 and performs processing for assisting a user in acquiring satisfactory volume data regardless of skills of the user. Since this assistance processing is substantially the same as the assistance processing in the first embodiment, duplicate description is omitted.

In the second embodiment, it is enough for the processing circuitry 57 (FIG. 12) of the ultrasonic diagnostic apparatus 10 to implement a function of controlling the entirety of the ultrasonic diagnostic apparatus 10. Thus, it is not necessarily required in the second embodiment that the processing circuitry 57 of the ultrasonic diagnostic apparatus 10 implements the image generation function 61, the indicator generation function 62, the display control function 63, and the assignment function 64.

In terms of operation and effect, the medical image processing apparatus 1A of the second embodiment functions in the same manner as the medical image processing apparatus 1 of the first embodiment by performing processing for assisting a user in acquiring satisfactory volume data regardless of skills of the user.

According to at least one of the above-described embodiments, it is possible to assist a user in acquiring satisfactory volume data regardless of skills of the user.

The processing circuitry 57 and the processing circuitry 57A in the above-described embodiments are examples of the processing circuitry recited in the claims.

The processing circuitry in the above-described embodiments is an example of the processing circuitry described in the claims. In addition, the term "processor" used in the explanation in the above-described embodiments, for instance, refer to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing corresponding program. When a plurality of processors are provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to
generate an image from volume data, the volume data being generated based on echo data acquired while the ultrasonic probe is moved and output of a positional sensor provided on the ultrasonic probe,
generate an indicator which indicates speed of the ultrasonic probe calculated based on the output of the positional sensor and a recommended speed range of moving the ultrasonic probe,
cause a display to display the image and the indicator,
generate three cross-sectional images corresponding to three respective cross-sections perpendicular to each other from the volume data,
generate three respective indicators for the three cross-sectional images in such a manner that the three respective indicators indicate distribution of acquisition density of the echo data in the respective three cross-sections, the acquisition density being obtained based on the output of the positional sensor, and
cause the display to display the three cross-sectional images and the three respective indicators in such a manner that the three respective indicators are composed with the three cross-sectional images.

2. The medical image processing apparatus according to claim 1, wherein the recommended speed range is determined according to a type of the ultrasonic probe, a scan condition for acquiring the echo data, an imaging target part for acquiring the echo data, or an instruction from a user.

3. The medical image processing apparatus according to claim 1,
wherein the image is at least one of an MPR (Multi Planar Reconstruction) image, a surface rendering image, and a volume rendering image.

4. The medical image processing apparatus according to claim 1, wherein the processing circuitry is further configured to
generate the indicator in such a manner that the indicator includes a colored frame for the image, and
change color of the colored frame according to the speed of the ultrasonic probe or according to relationship between the speed of the ultrasonic probe and the recommended speed range of moving the ultrasonic probe.

5. A medical image processing apparatus comprising:
processing circuitry configured to
generate an image from volume data, the volume data being generated based on echo data acquired while the ultrasonic probe is moved and output of a positional sensor provided on the ultrasonic probe,
generate an indicator which indicates speed of the ultrasonic probe calculated based on the output of the positional sensor and a recommended speed range of moving the ultrasonic probe,
cause a display to display the image and the indicator,
generate at least one cross-sectional image corresponding to at least one cross-section from the volume data,
generate another indicator indicating distribution of acquisition density of the echo data in the at least one cross-section, the acquisition density being obtained based on the output of the positional sensor, and
cause the display to display the at least one cross-sectional image and the another indicator in such a manner that the another indicator is composed with the at least one cross-sectional image, wherein the processing circuitry is further configured to
generate the another indicator indicating distribution of acquisition density of the echo data in such a manner that the another indicator includes a colored frame for the image, and
change color of the colored frame according to the distribution of acquisition density of the echo data.

6. A medical image processing apparatus comprising:
processing circuitry configured to generate at least one cross-sectional image corresponding to at least one cross-section from volume data, the volume data being generated based on echo data acquired while the ultrasonic probe is moved and output of a positional sensor provided on an ultrasonic probe,
assign, to each voxel of the volume data, information indicating uniformity of acquisition density of the echo-data, the acquisition density being obtained based on the output of the positional sensor,
generate an indicator based on the information indicating the uniformity of acquisition density of the echo-data assigned to the each voxel corresponding to the at least one cross-section in the volume data, and
cause a display to display the at least one cross-sectional image and the indicator in such a manner that the indicator is composed with the at least one cross-sectional image.

7. The medical image processing apparatus according to claim 6, wherein the processing circuitry is further configured to obtain the information indicating uniformity of acquisition density of the echo-data using respective acquisition densities of echo data which are related to respective three directions perpendicular to each other.

8. The medical image processing apparatus according to claim 1, wherein the processing circuitry is further configured to generate the volume data based on the echo data and the output of the positional sensor.

9. An ultrasonic diagnostic apparatus comprising the medical image processing apparatus according to claim 1.

10. A medical image processing method comprising:
generating an image from volume data, the volume data being generated based on echo data acquired while the ultrasonic probe is moved and output of a positional sensor provided on the ultrasonic probe;
generating an indicator which indicates speed of the ultrasonic probe calculated based on the output of the positional sensor and a recommended speed range of moving the ultrasonic probe; and
causing a display to display the image and the indicator, wherein
the step of generating the image from the volume data comprises generating three cross-sectional images corresponding to three respective cross-sections perpendicular to each other from the volume data,
the step of generating the indicator comprises further generating three respective indicators for the three cross-sectional images in such a manner that the three respective indicators indicate distribution of acquisition density of the echo data in the respective three cross-sections, the acquisition density being obtained based on the output of the positional sensor, and the causing step comprises causing the display to display the three cross-sectional images and the three respective indicators in such a manner that the three respective indicators are composed with the three cross-sectional images.

\* \* \* \* \*